United States Patent [19]

Takeuchi et al.

[11] Patent Number: 4,956,504
[45] Date of Patent: Sep. 11, 1990

[54] NOVEL SPERGUALIN-RELATED COMPOUNDS AND PROCESS FOR PRODUCING THE SAME

[75] Inventors: Tomio Takeuchi, Tokyo; Tetsushi Saino, Yono, both of Japan; Masao Yoshida, Hastings-on-Hudson, N.Y.; Katsutoshi Takahashi, Tokyo; Teruya Nakamura, Kusatsu, both of Japan; Hamao Umezawa, deceased, late of Tokyo, by Mieko Umezawa, Kazuo Umezawa, Yoji Umezawa, adminstrators

[73] Assignee: Zaidan Hojin Biseibutsu Kagaku Kenkyu Kai, Tokyo, Japan

[21] Appl. No.: 32,811

[22] Filed: Apr. 1, 1987

[30] Foreign Application Priority Data

Apr. 4, 1986 [JP] Japan ................. 61-77747

[51] Int. Cl.$^5$ ........................... C07C 129/12
[52] U.S. Cl. ..................... 564/153; 260/404.5; 562/439; 562/556; 562/560; 530/331; 548/537; 548/344; 548/496; 548/518
[58] Field of Search .............. 564/153; 562/439, 560, 562/426, 556; 548/537, 344, 496, 518; 530/331; 260/404.5 PA; 514/616, 20, 563, 562, 423, 400, 419, 18

[56] References Cited

U.S. PATENT DOCUMENTS

| | | | |
|---|---|---|---|
| 4,416,899 | 11/1983 | Umezawa et al. | 424/320 |
| 4,430,346 | 2/1984 | Umezawa et al. | 424/311 |
| 4,518,532 | 5/1985 | Umezawa et al. | 564/157 |
| 4,525,299 | 6/1985 | Umezawa et al. | 260/112.5 R |
| 4,529,549 | 7/1985 | Umezawa et al. | 260/404.5G |
| 4,556,735 | 12/1985 | Umezawa et al. | 564/187 |
| 4,710,517 | 12/1987 | Umezawa et al. | 514/616 |

FOREIGN PATENT DOCUMENTS

104099 6/1985 Japan ..................... 562/560

OTHER PUBLICATIONS

Umezawa et al., 13th *International Congress of Chemotherapy* (1983), pp. 76–77.

Takekuchi et al., *The Journal of Antibiotics*, vol. 34, No. 12 (1981), pp. 1619–1627.
Umezawa et al., *The Journal of Antibiotics*, vol. 38, No. 2 (1985), pp. 283–284.
Umeda et al., *The Journal of Antibiotics*, vol. 38, No. 7 (1985), pp. 886–898.

Primary Examiner—Carolyn S. Elmore
Attorney, Agent, or Firm—Banner, Birch, McKie & Beckett

[57] ABSTRACT

The present invention relates to novel Spergualin-related compounds represented by the general formula [I]

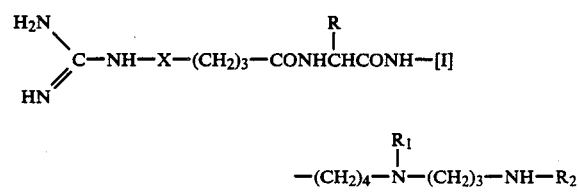

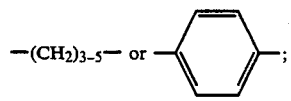

(wherein X is

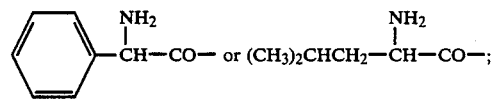

R is —H or —CH$_2$OH; R$_1$ is —H, $$\underset{\text{CH—CO—}}{\overset{\text{NH}_2}{\underset{|}{\text{C}_6\text{H}_5\text{—}}}} \text{ or } (CH_3)_2CHCH_2\underset{\text{CH—CO—}}{\overset{\text{NH}_2}{\underset{|}{\text{—}}}};$$

R$_2$ is a residue obtained by removing, from an amino acid or peptide, the hydroxyl group of the carboxyl group and, when R$_1$ is a group other than —H, R$_2$ is same as R$_1$), or a pharmacologically acceptable salt thereof. Said compounds or salts thereof have an immuno-modulating action.

10 Claims, No Drawings

NOVEL SPERGUALIN-RELATED COMPOUNDS AND PROCESS FOR PRODUCING THE SAME

BACKGROUND OF THE INVENTION

Spergualin is an antibiotic found by Umezawa (one of the present inventors) et. al. (U.S. Pat. No. 4,416,899). Since its discovery, many Spergualin-related compounds have been synthesized by Umezawa et. al. (U.S. Pat. No. 4,529,549, U.S. Pat. No. 4,556,735, etc.).

The compounds of the present invention have an immuno-modulating action with low toxicity and are expected as a medicine.

Conventional immuno-modulating agent generally have a strong side effect. Therefore, a compound having an excellent immuno-modulating action with reduced side effect and toxicity has been desired.

SUMMARY OF THE INVENTION

An object of the present invention is to provide an immuno-modulating agent (an immunosuppressive agent or immuno-stimulating agent) with reduced toxicity. Immunosuppressive agents are believed to be effective, for example, for the suppression of immunity required at the time of organ transplantation or as a thereapeutic agent for autoimmune diseases. Meanwhile, immuno-stimulating agents are believed to be useful for the cure of diseases caused by weakened immunity.

DETAILED DESCRIPTION OF THE INVENTION

As a result of extensive study, the present inventors found that novel Spergualin-related compounds represented by the general formula [I]

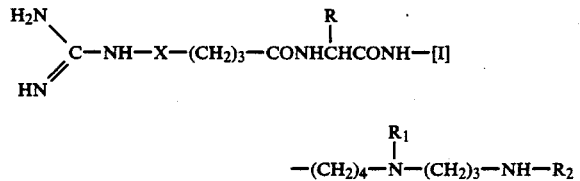

(wherein X is

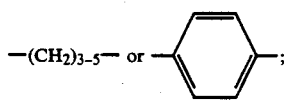

R is —H or —CH$_2$H; R$_1$ is —H,

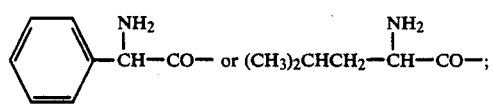

R$_2$ is a residue obtained by removing, from an amino acid or peptide, the hydroxyl group of the carboxyl group and, when R$_1$ is a group other than —H, R$_2$ is same as R$_1$) or pharmacologically acceptable salts thereof have an excellent activity, low toxicity and high safety. Based on this finding, the present invention has been completed.

As R$_2$ of the general formula [I], there can be mentioned a hydrogen atom and residues obtained by removing, from the following amino acids or peptides, the hydroxyl groups of the carboxyl groups. It is to be noted that the stereochemical configuration of these amino acid residues is L, D or DL except glycine, β-alanine and γ-aminobutyric acid.

(1) Amino acids

Alanine, arginine, ornithine, aspartic acid, asparagine, cysteine, cystine, glutamic acid, glutamine, pyroglutamic acid, glycine, histidine, lysine, proline, hydroxyproline, isoleucine, leucine, methionine, phenylalanine, phenylsubstituted phenylalanine, serine, threonine, tryptophane, homoserine, tyrosine, valine, phenylglycine, p-hydroxyphenylglycine, 4-hydroxymethyl-3-hydroxyphenylglycine, 8-alanine, γ-aminobutyric acid, 3-amino-2-hydroxy-4-phenylbutyric acid, etc.

(2) Peptides

As peptides, di- or tripeptides wherein two to three same or different amino acids mentioned above are condensed are preferred. There are illustrated the following examples.

Alanylalanine, leucylleucine, valylvaline, phenylalanylphenylalanine, tyrosyltyrosine, phenylglycylphenylglycine, glycylglycine, isoleucylisoleucine, leucylphenylalanine, phenylalanylleucine, leucylphenylglycine, phenylglycylleucine, glycylglycylglycine, phenylglycylphenylglycylphenylglycine, phenylalanylphenylalanylphenylalanine, leucylleucylleucine, etc.

Preferable amino acids or peptides are, for example, phenylglycine, phenylalanine, leucine, aspartic acid, tryptophane and alanine, as well as peptides formed by the condensation of two to three of said amino acids. Phenylglycine, phenylalanine, leucylleucine, etc. are more preferable.

Typical examples of R$_2$ are shown below.

(1) A group represented by the formula

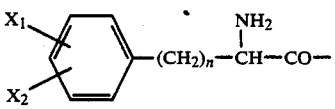

(wherein n is 0 or 1; X$_1$ is —H or —OH; and X$_2$ is —H or —CH$_2$OH).

(2) A group represented by the formula

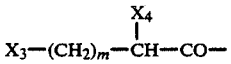

(wherein m is an integer of 0 to 4; X$_3$ is —H, —COOH, —OH, —NH$_2$ or —CONH$_2$; X$_4$ is —H or —NH$_2$; and at least one of X$_3$ and X$_4$ is —NH$_2$).

(3) A group represented by the formula

(wherein y is an integer of 1 or 2; A is

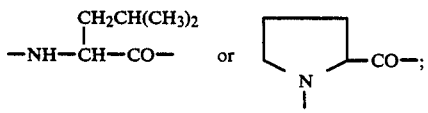

and, when y is 2, two As form a peptide linkage).

(4) A group represented by the formula

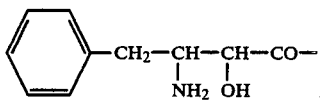

Preferable of the compounds represented by the general formula [I] or their pharmaceutically acceptable salts are, for example, such compounds as in the general formula [I], X is

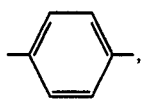

R is —CH$_2$OH, R$_1$ is

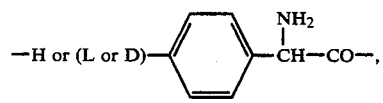

and R$_2$ is

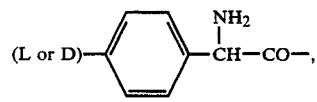

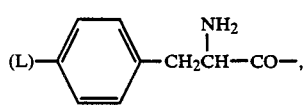

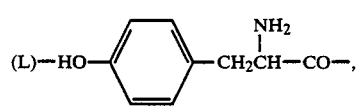

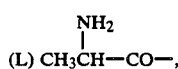

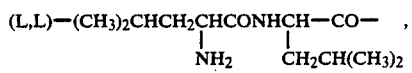

or pharmaceutically acceptable salts thereof.

The novel Spergualin-related compounds represented by the general formula [I] can form a salt with an acid. Such acid can be any inorganic or organic acid as long as it is nontoxic. There is no limitation for inorganic acids; however, hydrochloric acid, sulfuric acid, nitric acid, phosphoric acid, etc. are preferred. There is no limitation for organic acids, either; however, the preferred are acetic acid, propionic acid, succinic acid, fumaric acid, maleic acid, malic acid, tartaric acid, glutaric acid, citric acid, benzenesulfonic acid, toluenesulfonic acid, methanesulfonic acid, ethanesulfonic acid, propanesulfonic acid, aspartic acid, glutamic acid, etc.

Examples of the compounds of the general formula [I] according to the present invention are shown in Table 1. In the present specification, abbreviations have the following definitions.
TAD: triazadecane
GP: guanidinophenyl
GHep: guanidinoheptanoyl
For: 4-hydroxymethyl-3-hydroxyphenylglycyl
Amino acid residues
Ala alanyl
Leu: leucyl
Phe: phenylalanyl
Asp: aspartyl
Asn: asparaginyl
Lys: lysyl
PhG: phenylglycyl
Pro: prolyl
Tyr: tyrosyl
Ser: seryl
β-Ala: β-alanyl
AHPA: 3-amino-2-hydroxy-4-phenylbutyryl
Gly: glycyl
Glu: glutamyl
γ-ABA: γ-aminobutyryl Protective groups Z: benzyloxycarbonyl group
Boc: t-butyloxycarbonyl group
pMZ: p-methoxybenzyloxycarbonyl group
Aoc: t-amyloxycarbonyl group Amino acid residues containing protective groups Asp(OBzl): β-benzylaspartyl
Asp(OBu$^t$): β-t-butylaspartyl
Ser(Bzl): O-benzylseryl
Ser(Bu$^t$): O-t-butylseryl
Z-Lys: ε-benzyloxycarbonyllysyl
Tyr(Bu$^t$): O-t-butyltyrosyl

TABLE 1

$$H_2N\text{-}C(\text{=NH})\text{-}NH\text{-}X\text{-}(CH_2)_3\text{-}CONH\text{-}CH(R)\text{-}CONH(CH_2)_4\text{-}N(R_1)\text{-}(CH_2)_3\text{-}NH\text{-}R_2$$

| Compound No. | X | R | $R_1$ | $R_2$ | $R_2$ configuration |
|---|---|---|---|---|---|
| 1 | 1,4-phenylene | —CH$_2$—OH | H | PhG (Ph—CH(NH$_2$)—CO—) | L |
| 2 | " | " | " | Leu ((CH$_3$)$_2$CH—CH$_2$—CH(NH$_2$)—CO—) | L |
| 3 | " | " | " | Leu ((CH$_3$)$_2$CH—CH$_2$—CH(NH$_2$)—CO—) | D |
| 4 | " | " | " | PhG (Ph—CH(NH$_2$)—CO—) | D |
| 5 | " | " | " | Leu ((CH$_3$)$_2$CH—CH$_2$—CH(NH$_2$)—CO—) | L |
| 6 | " | " | " | Tyr (HO—C$_6$H$_4$—CH$_2$—CH(NH$_2$)—CO—) | L |
| 7 | " | " | " | Asp (HOOC—CH$_2$CH(NH$_2$)—CO—) | L |
| 8 | " | " | " | Ala (CH$_3$—CH(NH$_2$)CO—) | L |
| 9 | " | " | " | Ser (HO—CH$_2$—CH(NH$_2$)CO—) | L |
| 10 | " | " | " | Pro (pyrrolidine-2-CO—) | L |
| 11 | " | " | " | β-Ala (NH$_2$CH$_2$CH$_2$CO—) | — |
| 12 | " | " | " | AHPA (Ph—CH$_2$—CH(NH$_2$)—CH(OH)—CO—) | 2S, 3R |
| 13 | " | " | " | Leu—Leu (NH$_2$—CH(CH$_2$CH(CH$_3$)$_2$)—CO—NH—CH(CH$_2$CH(CH$_3$)$_2$)—CO—) | L, L |

TABLE 1-continued $$H_2N-C(=NH)-NH-X-(CH_2)_3-CONH-CH(R)-CONH(CH_2)_4-N(R_1)-(CH_2)_3-NH-R_2$$

| Compound No. | X | R | R₁ | R₂ | R₂ configuration |
|---|---|---|---|---|---|
| 14 | " | " | PhG: C₆H₅-CH(NH₂)-CO- (configuration: L) | PhG: C₆H₅-CH(NH₂)-CO- | L |
| 15 | " | " | H | Asn: H₂NOC-CH₂-CH(NH₂)-CO- | L |
| 16 | " | -CH₂OH | " | Lys: H₂NCH₂CH₂CH₂CH₂-CH(NH₂)-CO- | L |
| 17 | " | H | " | Leu: (CH₃)₂CH-CH₂-CH(NH₂)-CO- | L |
| 18 | " | " | " | PhG: C₆H₅-CH(NH₂)-CO- | L |
| 19 | -(CH₂)₃- | " | " | Leu: (CH₃)₂CH-CH₂-CH(NH₂)-CO- | L |
| 20 | " | " | " | PhG: C₆H₅-CH(NH₂)-CO- | L |
| 21 | " | -CH₂OH | " | Leu: (CH₃)₂CH-CH₂-CH(NH₂)-CO- | L |
| 22 | " | " | " | PhG: C₆H₅-CH(NH₂)-CO- | L |
| 23 | -C₆H₄- (para) | " | " | For: HO-C₆H₃(CH₂OH)-CH(NH₂)-CO- | DL |
| 24 | " | " | " | Pro—Pro— | L, L |
| 25 | -(CH₂)₃- | " | " | γ-ABA: NH₂(CH₂)₃CO- | |
| 26 | " | " | " | NH₂CH₂CO- | |

TABLE 1-continued $$\underset{HN}{\overset{H_2N}{>}}C-NH-X-(CH_2)_3-CONH-\underset{R}{\overset{|}{CH}}-CONH(CH_2)_4-\underset{R_1}{\overset{|}{N}}-(CH_2)_3-NH-R_2$$

| Compound No. | X | R | R₁ | R₂ | R₂ config- uration |
|---|---|---|---|---|---|
| | | | | (Gly) | |
| 27 | " | " | " | HO—CH₂—CHCO— <br> \| <br> NH₂ (Ser) | L |
| 28 | " | " | NH₂CHCO— <br> \| <br> (CH₂)₂COOH (Glu) | NH₂ <br> \| <br> (CH₃)₂CHCH₂CHCO— <br> (Leu) | L |

Of the compounds shown in Table 1, the preferable are Compound Nos. 1, 2, 4 to 8, 13 and 14. More preferable are Compound Nos. 1, 2, 5, 13 and 14.

The compounds of the general formula [I] can be synthesized by removing protecting groups from a protecting group-containing compound represented by the general formula [II]

ple, when the removal of protecting group is conducted by catalytic reduction using palladium black, the reaction mixture is filtered to remove the catalyst; the filtrate is concentrated under vacuum; and the residue is purified by a known purification method using CM-Sephadex ® (Na⁺) and Sephadex ® LH-20 [T. Takeuchi et al., J. Antibiotics, 34, 1619 (1981)] to obtain a

[II]

[wherein X is

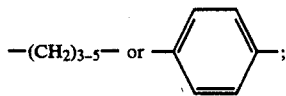

$R_3$ is —H or —CH$_2$—O—Y (wherein Y is —H or a protecting group for —OH); $R_4$ is —H, a phenylglycyl group wherein the amino group is protected, or a leucyl group wherein the amino group is protected; and $R_5$ is a residue obtained by removing, from an amino acid or peptide having protected amino groups, the hydroxyl group of the carboxyl group (the side chains of the residue may be protected) and, when $R_4$ is a phenylglycyl group wherein the amino group is protected or a leucyl group wherein the amino group protected, $R_5$ is a phenylglycyl or leucyl group wherein the amino group is protected.].

The removal of protecting groups can be conducted by means such as reduction, acid decomposition, hydrolysis or the like.

The reaction for removal of protecting groups is ordinarily conducted in an inert solvent at temperatures from −60° C. to the boiling point of the solvent, preferably from about −50° C. to about 100° C. As the inert solvent, there can be used water as well as hydrophilic organic solvents such as lower alcohols (e.g. methanol, ethanol), ketones (e.g. acetone, methyl ethyl ketone), amides (e.g. dimethylformamide, dimethylacetamide), cyclic ethers (e.g. tetrahydrofuran, dioxane), lower fatty acids (e.g. acetic acid, trifluoroacetic acid), liquid ammonia, liquid hydrogen fluoride and the like.

After the completion of the reaction for removal of protecting group, the reaction mixture is subjected to the following purification to isolate a novel Spergualin-related compound of the general formula [I]. For examdesired compound. When the removal of protecting group is conducted using trifluoroacetic acid, the reaction mixture is concentrated under vacuum and the residue is purified by the same purification method as mentioned above to obtain a desired compound.

In the above purification, the novel Spergualin-related compound of the general formula [I] is obtained as a hydrochloride. This hydrochloride can be converted to other salt according to, for example, one of the following procedures. The hydrochloride is dissolved in water; the aqueous solution is passed through a strongly basic ion exchange resin to collect a fraction containing a desired compound; to the fraction is added a desired acid, an aqueous solution containing the acid, or a solution of the acid dissolved in a hydrophilic organic acid (e.g. methanol, ethanol, acetone, tetrahydrofuran, dioxane) to effect neutralization; and the neutralization mixture is subjected to dryness under vacuum or, when containing an organic solvent, is subjected to vacuum distillation to remove the solvent and then to lyophilization. Alternatively, the hydrochloride is mixed with silver hydroxide or an aqueous silver oxide solution to neutralize the hydrogen chloride of the hydrochloride; the reaction mixture is filtered to the insoluble silver chloride; the filtrate is mixed with a desired acid to form a slat; and the reaction mixture is subjected to lyophilization.

The salt other than hydrochloride, obtained as above may take a form of hydrate, depending upon the treating conditions.

The protected Spergualin-related compounds of the general formula [II] used as a starting material in the present invention can be synthesized as follows.

(a) Synthesis of compound of the general formula [II] wherein $R_4$ is a hydrogen atom and $R_5$ is a residue obtained by removing, from an amino acid having protected amino groups, the hydroxyl group of the carboxyl group (the side chains of the residue may be protected).

A Spergualin-related compound represented by the general formula [III].

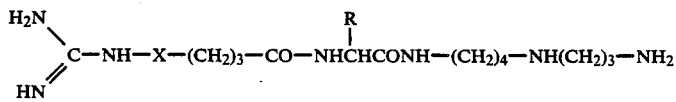

[III]

(wherein X and R each have the same definition as given previously) which is obtained according to a process described in Japanese Patent Application Kokai (Laid-Open) Nos. 42356/1984 and 185758/1985 is condensed with an N-protected-α- or ω-amino acid represented by the general formula [IV]

$R_5'$—OH [IV]

[wherein $R_5'$ is a residue obtained by removing, from an amino acid having protected amino groups, the hydroxyl group of the carboxyl group (the side chains of the residue may be protected)] or a reactive derivative thereof to obtain a titled compound (b) Synthesis of compounds of the general formula [II] wherein $R_4$ is a hydrogen atom and $R_5$ is a residue obtained by removing, from a peptide having protected amino groups, the hydroxyl group of the carboxyl group (the side chains of the residue may be protected).

A compound of the general formula [III] is condensed with a first N-protected amino acid or a reactive derivative thereof and then the N-protecting group is removed; the resulting compound is condensed with a second N-protected amino acid or a reactive derivative thereof and then the N-protecting group is removed; whereby, a compound of the general formula [II] wherein $R_5$ is a residue obtained by removing, from an N-protected dipeptide, the hydroxyl group of the carboxyl group can be obtained.

When the compound of the general formula [II] is further condensed with a third N-protected amino acid and the N-protecting group is removed, a compound of the general formula [II] wherein R is a residue obtained by removing, from an N-protected tripeptide, the hydroxyl group of the carboxyl group, can be obtained.

(c) Synthesis of compounds of the general formula [II] wherein both $4_R$ and $R_5$ are an N-protected phenylglycyl group or N-protected leucyl group.

A compound represented by the general formula [V]

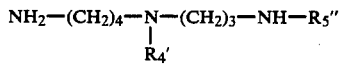 [V]

(wherein both $R_4'$ and $R_5'$ are an N-protected phenylglycyl group or an N-protected leucyl group) is condensed with a protected amino acid represented by the general formula [VI]

 [VI]

(wherein $P_2$ is a protecting group and $R_3$ has the same definition as given previously) or a reactive derivative thereof to obtain a compound represented by the general formula [VII]

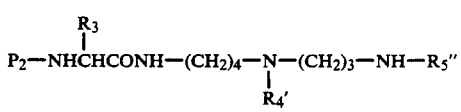 [VII]

(wherein $P_2$, $R_3$, $R_4'$ and $R_5''$ each have the same definition as given previously). Then, the protecting group $P_2$ is removed selectively, and the resulting compound is condensed with an ω-guanidino acid derivative represented by the general formula [VIII]

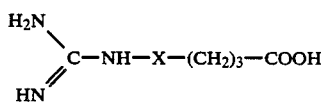 [VIII]

(wherein X has the same definition as given previously) or a reactive derivative thereof to obtain a titled compound.

For information, the compound of the general formula [V] can be produced according to the following ordinary process.

For instance, 1 mole of an N-protected spermidine represented by the general formula [IX]

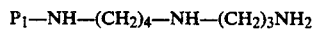 [IX]

(wherein $P_1$ has the same definition as given previously) is condensed with 1 mole of a reactive derivative obtained from the reaction of an N-protected amino acid of the general formula [IV]

 [IV]

(wherein $R_5''$ has the same definition as given previously) and 1,3-thiazolidine-2-thione; the condensation product is then reacted with an N-protected amino acid represented by the general formula [X]

 [X]

[wherein $R_4'$ is a residue obtained by removing —OH from an amino acid having protected amino groups (the side chains of the amino acid may be protected)]; subsequently, the protecting group $P_1$ is removed selectively to obtain a compound of the general formula [V].

When $R_4'$ and $R_5''$ are same, the compound of the general formula [V] can also be produced by reacting 1 mole of an N-protected spermidine of the general formula [IX] with at least 2 moles of a protected amino acid of the general formula [IV] or [X] or a reactive derivative thereof and then selectively removing the protecting group $P_1$ from the reaction product.

The N-protected spermidine of the general formula [IX] can be produced by reacting a compound represented by the general formula [XI]

 [XI]

(wherein P₁ has the same definition as given previously) with acrylonitrile and then reducing the nitrile group.

The condensation in the above (a), (b) and (c) can be conducted in accordance with an ordinary method used for peptide linkage formation. The method includes a carbodiimide method using dicyclohexylcarbodiimide, 1-ethyl-3-(N,N-dimethylaminopropyl)carbodiimide, etc.; an azide method using hydrazide, etc.; a mixed acid anhydride method using ethyl chlorocarbonate, isobutyl chlorocarbonate, etc.; an active ester method using a cyanomethyl ester, a vinyl ester, a substituted or unsubstituted phenyl ester, a thiophenyl ester, a hydroxysuccinimide ester, etc.; an o-acylhydroxylamine derivative method using acetoxime, cyclohexanoxime, etc.; an N-acyl compound method using carbonyldiimidazole, etc.; and a carboxylic acid activation method using 1,3-thiazolidine-2-thione.

The solvent used in the condensation can be those used in ordinary reaction of peptide linkage formation. As the solvent, there can be mentioned, for example, ethers such as diethyl ether, tetrahydrofuran and the like; esters such as ethyl acetate and the like; ketones such as acetone, methyl ethyl ketone and the like; halogenated hydrocarbons such as methylene chloride, chloroform and the like; amides such as dimethylformamide, dimethylacetamide and the like; and nitriles such as acetonitrile and the like. These solvents can be used singly or, when they are miscible with water, as a mixed solvent with water.

The protecting groups for amino groups, used in the present invention includes benzyloxycarbonyl group, substituted benzyloxycarbonyl group (e.g. p-methoxybenzyloxycarbonyl group), t-butyloxycarbonyl group, t-amyloxycarbonyl group, formyl group, trityl group, o-nitrophenylsulfenyl group, etc.

The protecting group for side chains of amino acid can be as follows. The protecting group for carboxyl group includes lower alkyl group, t-butyl group, benzyl group and substituted benzyl group; the protecting group for hydroxyl group includes t-butyl group and benzyl group; the protecting group for mercapto group includes benzyl group and p-methoxybenzyl group; the protecting group for imidazole group includes benzyloxycarbonyl group, benzyl group and tosyl group; and the protecting group for guanidino group includes nitro group, tosyl group and t-butyloxycarbonyl group. However, the protecting group for the side chains of amino acid is not restricted to those mentioned above.

Typical examples of the compound of the general formula [II] used as a starting material in the present invention are shown in Table 2. The stereochemical configuration of amino acid residue is L, D or LD

Amino acid residues

Ala: alanyl
Leu: leucyl
Phe: phenylalanyl
Asp: aspartyl
Asn: asparaginyl
Lys: lysyl
PhG: phenylglycyl
Pro: prolyl
Tyr: tyrosyl
Ser: seryl
β-Ala: β-alanyl
AHPA: 3-amino-2-hydroxy-4-phenylbutyryl
Gly: glycyl
Glu: glutamyl
γ-ABA: γ-aminobutyryl

Protective groups

Z: benzyloxycarbonyl group
Boc: t-butyloxycarbonyl group
pMZ: p-methoxybenzyloxycarbonyl group
Aoc: t-amyloxycarbonyl group

Amino acid residues containing protective groups

Asp(OBz): β-benzylaspartyl
Asp(OBuᵗ): β-t-butylaspartyl
Ser(Bzl): O-benzylseryl
Ser(Buᵗ): O-t-butylsesryl
Z-Lys: ε-benzyloxycarbonyllysyl
Tyr(Buᵗ): O-t-butyltyrosyl

TABLE 2

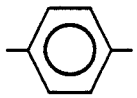

Typical examples of the compound represented by the general formula [II]

$$H_2N\diagdown_{HN}\!\!=\!\!C-NH-X-(CH_2)_3-CONHCH(R_3)-CONH-(CH_2)_4-N(R_4)-(CH_2)_3-NH-R_5$$

| X | R₃ | R₄ | R₅ |
|---|----|----|----|
| ⟨phenyl⟩ | —CH₂OH | H | Z—Leu— |
| " | " | " | Boc—Leu— |
| " | " | " | pMz—Leu— |
| " | " | " | Z—PhG— |
| " | " | " | Boc—PhG— |
| " | " | " | pMz—PhG— |
| " | " | " | Z—Phe— |
| " | " | " | Boc—Phe— |
| " | " | " | pMz—Phe— |
| " | " | " | Z—Tyr— |
| " | " | " | Aoc—Tyr(Buᵗ)— |
| " | " | " | pMz—Tyr(Buᵗ)— |
| " | " | " | Z—Asp(OBzl)— |
| " | " | " | Boc—Asp(OBuᵗ)— |
| " | " | " | pMz—Asp(OBuᵗ)— |
| " | " | " | Z—Ala— |
| " | " | " | Boc—Ala— |

TABLE 2-continued

Typical examples of the compound represented by the general formula [II]

$$\begin{array}{c}H_2N\\ \phantom{H_2}\diagdown\\ HN\diagup\end{array}C-NH-X-(CH_2)_3-CONHCH-CONH-(CH_2)_4-N-(CH_2)_3-NH-R_5$$
with $R_3$ on the CH and $R_4$ on the N.

| X | $R_3$ | $R_4$ | $R_5$ |
|---|---|---|---|
| " | " | " | pMz—Ala— |
| " | " | " | Z—Ser(Bzl)— |
| " | " | " | Boc—Ser(Bu$^t$)— |
| " | " | " | pMz—Ser(Bu$^t$)— |
| " | " | " | Z—Pro— |
| " | " | " | Boc—Pro— |
| " | " | " | pMz—Pro— |
| " | " | " | Z—Asn— |
| " | " | " | Boc—Asn— |
| " | " | " | pMz—Asn— |
|  | —CH$_2$OH | " | Z\|<br>Z—Lys— |
| " | " | " | Z\|<br>Boc—Lys— |
| " | " | " | Z\|<br>pMz—Lys— |
| " | " | " | Z—Leu—Leu— |
| " | " | " | Boc—Leu—Leu— |
| " | " | " | pMz—Leu—Leu— |
| " | " | " | Z—PhG—PhG— |
| " | " | " | Boc—PhG—PhG— |
| " | " | " | pMz—PhG—PhG— |
| " | " | " | Z—β—Ala— |
| " | " | " | Boc—β—Ala— |
| " | " | " | pMz—β—Ala— |
| " | " | " | Z—AHPA— |
| " | " | " | Boc—AHPA— |
| " | " | " | pMz—AHPA— |
| " | H | " | Z—Leu— |
| " | " | " | Boc—Leu— |
| " | " | " | pMz—Leu— |
| " | " | " | Z—PhG— |
| " | " | " | Boc—PhG— |
| " | " | " | pMz—PhG— |
|  | H | H | Z—Leu—Leu— |
| " | " | " | Boc—Leu—Leu— |
| " | " | " | pMZ—Leu—Leu— |
| " | H | " | Z—Phe— |
| " | " | " | Boc—Phe— |
| " | " | " | pMz—Phe— |
| ⁺(CH$_2$)$_3$ | —CH$_2$OH | " | Z—Leu— |
| " | " | " | Boc—Leu— |
| " | " | " | pMz—Leu— |
| " | " | " | Z—PhG— |
| " | " | " | Boc—PhG— |
| " | " | " | pMz—PhG— |
| " | " | " | Z—Leu—Leu— |
| " | " | " | Boc—Leu—Leu— |
| " | " | " | pMz—Leu—Leu— |
| " | " | " | Z—GABA |
| " | " | " | Z—Gly |
| " | " | " | Boc—Asp (OB$_2$l) |
| " | H | " | Z—Leu—Leu— |
| " | " | " | Boc—Leu—Leu— |
| " | " | " | pMz—Leu—Leu— |
| " | " | " | Z—Leu— |
| " | " | " | Boc—Leu— |
| " | " | " | pMz—Leu— |
| ⁺(CH$_2$)$_3$ | H | H | Z—PhG— |

TABLE 2-continued

Typical examples of the compound represented by the general formula [II]

| X | R₃ | R₄ | R₅ |
|---|---|---|---|
| " | " | " | Boc—PhG— |
| " | " | " | pMz—PhG— |
| ⟨phenyl⟩ | —CH₂OBzl | Z—PhG— | Z—PhG— |
| " | —CH₂—OBuᵗ | Boc—PhG— | Boc—PhG— |
| " | " | pMz—PhG— | pMz—PhG— |
| " | —CH₂OBzl | Z—Leu— | Z—Leu— |
| " | —CH₂OBuᵗ | Boc—Leu— | Boc—Leu— |
| " | " | pMz—Leu— | pMz—Leu— |
| " | —CH₂OBzl | Z—Leu—Leu— | Z—Leu—Leu— |
| " | —CH₂OBuᵗ | Boc—Leu—Leu— | Boc—Leu—Leu— |
| " | " | pMz—Leu—Leu— | pMz—Leu—Leu— |
| " | H | Z—PhG— | Z—PhG— |
| " | " | Boc—PhG— | Boc—PhG— |
| " | " | pMz—PhG— | pMz—PhG— |
| ⟵CH₂⟶₃ | " | Z—PhG— | Z—PhG— |
| " | " | Boc—PhG— | Boc—PhG— |
| " | " | pMz—PhG— | pMz—PhG— |
| " | —CH₂OBzl | Z—PhG— | Z—PhG— |
| " | —CH₂OBuᵗ | Boc—PhG— | Boc—PhG— |
| " | " | pMz—PhG— | pMz—PhG— |

In using the present compounds as a medicine, they are made into a desired preparation according to an ordinary method, using, if necessary, an excipient and can be administered orally or parenterally.

When an injection is prepared, it is advisable that the injection ordinarily contain 0.1 to 30% by weight, preferably 1 to 10% by weight of an active ingredient. In oral administration, a tablet, a capsule, a powder, a granule, a liquid, a dry syrup, etc. are used. The capsule, the granule and the powder generally contains 5 to 100% by weight, preferably 25 to 100% by weight of an active ingredient.

The amount of administration is determined by the age and weight of patient, the condition of disease, the purpose of cure, etc. but generally is 1 to 100 mg/kg/day in parenteral administration and 5 to 500 mg/kg/day in oral administration.

Next, the toxicity and physiological activity of the present compound will be shown by experiments.

1. Methods of experiments

(a) Toxicity

A compound of the present invention was dissolved in a physiological saline solution in various concentrations. Each of the resulting solutions was intraperitoneally administered to one of CDF₁-SLC female mice (one group: two to three mice) in an amount of 0.1 ml per 10 g of body weight. The highest concentration of present compound in solution was 400 mg/10 ml/kg, and starting from this solution of highest concentration, solutions of lower concentrations were prepared each time at a common ratio of 2. The administration amount of present compound with the lowest concentration solution with which at least one mouse died was taken as an administration amount of acute toxicity.

(b) Inhibitory activity against antibody formation

Test groups and a control group of CDF₁-SLC female mice (each group: five mice) were intravenously sensitized with $1 \times 10^8/0.2$ ml of sheep red blood cells (SRBC). A compound of the present invention was dissolved in a physiological saline solution in various concentrations. Each of the resulting solutions was administered to one of the test groups once a day for three consecutive days from the next day of the sensitization, in an amount of 0.1 ml/10 g (body weight)/day. The physiological saline solution was administered to the control group.

In the fourth day from the sensitization, all the mice were killed and the number of anti-SRBC plaque-forming cells (PFC) in the spleen cells of each mouse was measured. From this number, the PFC number per $10^6$ of spleen cells was calculated. The effect of the present compound was expressed as an inhibition percentage (%) of PFC number of test group as compared with control group.

Inhibition percentage (%) =

[1 − (*PFC* number of test group)/

(*PFC* number of control group)] × 100

3. Life prolongation effect of present compound to mouse leukemia cells L1210 and its toxicity $1 \times 10^5/0.2$ ml/mouse of mouse leukemia cells L1210 were intraperitoneally transplanted to test groups and a control group of CDF₁-SLC female mice (each group: four mice). A compound of the present invention was dissolved in a physiological saline solution in various concentrations and each of the resulting solutions was administered to one of the test groups once a day for nine consecutive days from the next day of the transplantation, in an amount of 0.1 ml/10 g (body weight)/day. The physiological saline solution was administered to the control group.

All the mice of the test groups and the control group were observed from the next day of the L1210 transplantation to examine their days of survival, and the average days of survival (T) of each test group and the average days of survival (C) of the control group were calculated. The life prolongation percentage of the present compound was expressed as (T/C)×100.

It is believed that a (T/C)×100 of 125 or more is effective.

2. Results of experiments

The administration amounts of present compounds causing acute death when administered to mice are shown in Table 3. The inhibitory actions for antibody formation, of typical compounds of the present invention are shown in Table 4. The antitumor activities of typical compounds of the present invention are shown in Table 5. In Tables and 5, a control compound is included. This compound is such that in the general formula [I], X is

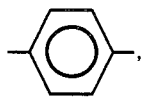

R is —CH$_2$OH and both of R$_1$ and R$_2$ are —H.

TABLE 3
Administration amounts of present compounds causing acute death to mice

| Compound No. | Administration amount (mg/kg) |
|---|---|
| 1 | 100 |
| 3 | 100 |
| 4 | 100 |
| 5 | 100 |
| 6 | 100 |
| 7 | 100 |
| 9 | >100 |
| 10 | 100 |
| 12 | 100 |
| 13 | 100 |
| 14 | 200 |

TABLE 4
Inhibitory activities against antibody formation, of present compounds

| Compound No. | Inhibitory percentage Administration amount 1.56 mg/kg | Administration amount 6.25 mg/kg |
|---|---|---|
| 1 | 87 | 97 |
| 2 | 60 | 92 |
| 4 | 68 | 95 |
| 13 | 53 | 88 |
| 14 | −50* | −75* |
| Control | 39 | 86 |

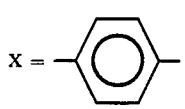

R = —CH$_2$OH

TABLE 4-continued
Inhibitory activities against antibody formation, of present compounds

| Compound No. | Inhibitory percentage Administration amount 1.56 mg/kg | Administration amount 6.25 mg/kg |
|---|---|---|
| R$_1$ = R$_2$ = H | | |

*— (minus) shows an increase of antibody formation.

TABLE 5
Life prolongation effect of present compounds to mouse leukemia L1210

| Compound No. | Administration amount mg/kg/day | T/C × 100 (%) |
|---|---|---|
| 1 | 50.00 | 327 |
|  | 25.00 | 294 |
|  | 12.50 | 278 |
|  | 6.25 | 315 |
|  | 3.13 | 269 |
|  | 1.56 | 296 |
|  | 0.78 | 195 |
|  | 0.39 | 146 |
| 2 | 50.00 | 53 |
|  | 25.00 | 281 |
|  | 12.50 | 272 |
|  | 6.25 | 300 |
|  | 3.13 | 331 |
|  | 1.56 | 244 |
|  | 0.78 | 152 |
|  | 0.39 | 136 |
| 4 | 50.00 | 197 |
|  | 25.00 | 247 |
|  | 12.50 | 243 |
|  | 6.25 | 237 |
|  | 3.13 | 228 |
|  | 1.56 | 195 |
|  | 0.78 | 149 |
|  | 0.39 | 125 |
| 5 | 50.00 | 253 |
|  | 25.00 | 284 |
|  | 12.50 | 290 |
|  | 6.25 | 290 |
|  | 3.13 | 265 |
|  | 1.56 | 146 |
|  | 0.78 | 133 |
|  | 0.39 | 123 |
| 6 | 50.00 | 162 |
|  | 25.00 | 270 |
|  | 12.50 | 250 |
|  | 6.25 | 250 |
|  | 3.13 | 267 |
|  | 1.56 | 201 |
|  | 0.78 | 158 |
|  | 0.39 | 125 |
| 7 | 50.00 | 284 |
|  | 25.00 | 284 |
|  | 12.50 | 265 |
|  | 6.25 | 216 |
|  | 3.13 | 152 |
|  | 1.56 | 99 |
|  | 0.78 | 86 |
|  | 0.39 | 96 |
| 8 | 25.00 | 362 |
|  | 12.50 | 290 |
|  | 6.25 | 272 |
|  | 3.13 | 312 |
|  | 1.56 | 164 |
|  | 0.78 | 130 |
|  | 0.39 | 102 |
|  | 0.20 | 109 |
| 9 | 100.00 | 103 |
|  | 50.00 | 250 |
|  | 25.00 | 241 |
|  | 12.50 | 276 |
|  | 6.25 | 191 |
|  | 3.13 | 155 |
|  | 1.56 | 125 |
|  | 0.78 | 118 |

TABLE 5-continued

Life prolongation effect of present compounds to mouse leukemia L1210

| Compound No. | Administration amount mg/kg/day | T/C × 100 (%) |
| --- | --- | --- |
| 13 | 50.00 | 303 |
|  | 25.00 | 274 |
|  | 12.50 | 257 |
|  | 6.25 | 247 |
|  | 3.13 | 283 |
|  | 1.56 | 201 |
|  | 0.78 | 149 |
|  | 0.39 | 132 |
| Control 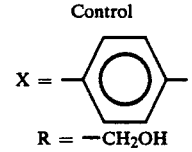 $X = $  $R = -CH_2OH$ $R_1 = R_2 = H$ | 25.00 | 191 |
|  | 12.50 | 261 |
|  | 6.25 | 254 |
|  | 3.13 | 243 |
|  | 1.56 | 211 |
|  | 0.78 | 158 |
|  | 0.39 | 129 |
|  | 0.20 | 109 |

As is clear from the above experiments, the administration amounts of present compounds causing acute death are larger and accordingly they have higher safety. Moreover, the present compounds have excellent physiological activity. Therefore, the present compounds are expected as medicines such as an immunosuppressive agent and an antitumor agent. Of the present compounds, such compounds as $R_2$ of the general formula [I] is a neutral amino acid or a peptide consisting of neutral amino acids are preferred because of their excellent activities and low toxicity.

Next, the present invention will be explained concretely by way of Examples. In the Examples, the Rf value of TLC (thin layer chromatography) was obtained by using a silica gel 60 $F_{254}$ plate (thickness: 0.25 mm) manufactured by Merck Co., developing a sample containing a present compound for a distance of about 8 cm with a developing solution described later, measuring a distance from the starting point to a center of the spot of an intended compound (the present compound) and dividing the distance by a distance from the starting point to the front end of the developing solvent. Detections were carried out with ultraviolet absorption, or visualized with ninhydrin and a Sakaguchi reagent.

EXAMPLE 1

10-{N-[4-(4-GP)butanoyl]-L-Ser}-1-L-PhG-1,5,10-TAD trihydrochloride (compound No. 1)

0.76 g (0.98 mmol) of a white crystal of 10-{N-[4-(4-GP)butanoyl]-L-Ser}-1-(Z-L-PhG)-1,5,10-TAD dihydrochloride was dissolved in 30 ml of methanol. Thereto was added 0.15 g of palladium black. The mixture was subjected to catalytic reduction for 5 hr at room temperature at normal pressure.

After the reaction, the reaction mixture was filtered to remove the catalyst. The filtrate was concentrated under vacuum to obtain 0.7 g of an oily substance. (The yield was quantitative.)

This oily substance was dissolved in 6 ml of distilled water and subjected to chromatography on a column packed with 105 ml of CM-Sephadex ® C-25 (Na+). Then, elution was conducted in accordance with a gradient elution method from 500 ml of distilled water to 500 ml of an aqueous 1.0M sodium chloride solution to collect fractions containing a desired compound. These fractions were concentrated to dryness under vacuum. Methanol was added to the residue and the resulting solution was filtered to remove sodium chloride. The resulting oily substance was purified as follows to obtain a desired compound.

In order to remove a small amount of remaining sodium chloride, the oily substance was dissolved in 4 ml of methanol and subjected to chromatography on a column packed with 70 ml of Sephadex ® LH-20. Elution was conducted with methanol to collect fractions containing a desired compound. They were concentrated under vacuum. In order to further remove a slight amount of impurities, the resulting oily substance was dissolved in 4 ml of distilled water and subjected to column chromatography on a column packed with 70 ml of HP-20 ® (Mitsubishi Chemical Industries, Ltd.). Elution was conducted with distilled water to collect fractions containing a desired compound. The fractions were concentrated under vacuum. The resulting oily substance was dissolved in 5 ml of distilled water and the solution was filtered to remove insolubles. The filtrate was lyophilized to obtain 0.37 g (yield: 55.63%) of a desired compound.

NMR ($D_2O$, external TMS) $\delta = 1.6-4.0$ (m, 21H), 4.1–4.5 (d, 2H, J=5 Hz), 4.6–4.9 (t, H, J=5 Hz), 5.63 (s, H), 7.5–8.1 (m, 4H), 8.05 (s, 5H).

IR (KBr) $\nu$ (cm$^{-1}$) = 3325, 2950, 1650, 1510, 1250.

TLC (chloroform:methanol:aqueous 17% ammonia solution = 6:4:1 v/v) Rf=0.15.

$[\alpha]_D^{20} + 15.3°$ (C=1.03, $H_2O$).

In Examples 2 to 24, other compounds of the general formula [I] were produced from other compounds of the general formula [II] in manners similar to that of Example 1.

In Examples 2 to 24, if the amino protecting group of 1-amino acid of the compound represented by the general formula [II] was not benzyloxycarbonyl group but t-butyloxycarbonyl group, p-methoxybenzyloxycarbonyl group or t-amyloxycarbonyl group, and the protecting group for the carboxyl group or hydroxyl group was t-butyl group, the treatment for removal of protecting group was conducted not by catalytic reduction but by (a) trifluoroacetic acid or, when the compound of the general formula [II] contained both benzyloxycarbonyl group and t-butyl group, (b) catalytic reduction followed by trifluoroacetic acid; and the subsequent treatments were conducted in the same manner as in Example 1 to obtain respective desired compounds.

The results of Examples 2 to 24 are summarized in Table 6.

TABLE 6

| Example No. | Compound of general formula [II] | Compound of general formula [I] |
| --- | --- | --- |
| 2 | 10-{N-[4-(4-GP)butanoyl]-L-Ser}-1-(Z-L-Leu)-1,5,10-TAD 6:2.5:0.5 NMR ($D_2O$, external TMS) $\delta = 1.1-1.6$ (m, 6H), 1.7–4.0 (m, 6:2.5:0.5 external TMS) 4.1–5.0 (m, 4H), 5.53 (s, 2H), | 10-{N-[4-(4-GP)butanoyl]-L-Ser}-1-L-(Compound No. 2) $\delta = 1.2-1.7$ (b, 6H), 1.8–4.1 (m, 23H), |

TABLE 6-continued

| Example No. | Compound of general formula [II] | Compound of general formula [I] |
|---|---|---|
| | 7.4–14 8.1 (m, 4H), 7.81 (s, 5H), IR (KBr) $\nu$ (cm$^{-1}$) = 3290, 2965, 1650, 1520, 1445, 1250, 1040 TLC (chloroform : methanol : aqueous 17% ammonia solution = 6:4:1 v/v) Rf = 0.48 | 4.1–4.5 (m, 3H), 4.6–4.9 (t, H, J = 5Hz), 7.5–8.1 (m, 4H) IR (KBr) $\nu$ (cm$^{-1}$) = 3320, 2960, 1650, 1545, 1515, 1455, 1255 TLC (chloroform : methanol : aqueous 17% ammonia solution = 6:4:1 v/v) Rf = 0.19 $[\alpha]_D^{20}$ −7.9° (C = 1.05, H$_2$O) |
| 3 | 10-{N-[4-(4-GP)butanoyl]-L-Ser}-1-(Boc-D-Leu)-1,5,10-TAD dihydrochloride<br><br>NMR (D$_2$O, external TSM)<br>$\delta$ = 1.1–1.6 (m, 6H), 1.7–4.0 (m, 23H), 1.88 (s, 9H), 4.1–5.0 (m, 4H), 7.5–8.0 (m, 4H) | 10-{N-[4-(4-GP)butanoyl]-L-Ser}-1-D-Leu-1,5,10-TAD trihydrochloride (Compound No. 3)<br>IR (KBr)<br>$\nu$ (cm$^{-1}$) = 3330, 2960, 1645, 1515, 1455, 1255<br>$[\alpha]_D^{20}$ −19.0° (C = 1.15, H$_2$O) |
| 4 | 10-{N-[4-(4-GP)butanoyl]-L-Ser}-1-(Boc-D-Phe)-1,5,10-TAD dihydrochloride<br><br>NMR (D$_2$O, external TMS)<br>$\nu$ = 1.6–4.0 (m, 20H), 1.84 (s, 9H), 4.1–4.5 (d, 2H, J = 5Hz), 4.5–5.0 (t, H, J = 5Hz), 5.5 (s, H), 7.5–8.0 (m, 4H), 7.83 (s, 5H)<br>IR (KBr)<br>$\nu$ (cm$^{-1}$) = 3280, 2930, 1650, 1510, 1450, 1365, 1245, 1160, 1045<br>TLC (chloroform : methanol : aqueous 17% ammonia solution = 6:4:1 v/v)<br>Rf = 0.36 | 10-{N-[4-(4-GP)butanoyl]-L-Ser}-1-D-Phe-1,5,10-TAD trihydrochloride (Compound No. 4)<br>NMR (D$_2$O, external TMS)<br>$\delta$ = 1.7–4.0 (m, 21H), 4.1–4.5 (d, 2H, J = 5Hz), 4.6–4.9 (t, H, J = 5Hz), 5.63 (s, H), 7.5–8.1 (m, 4H), 8.05 (s, 5H)<br>IR (KBr)<br>$\nu$ (cm$^{-1}$) = 3290, 2950, 1650, 1510, 1450, 1250, 1055<br>TLC (chloroform : methanol : aqueous 17% ammonia solution = 6:4:1 v/v)<br>Rf = 0.15<br>$[\alpha]_D^{20}$ −10.5° (C = 1.0, H$_2$O) |
| 5 | 10-{N-[4-(4-GP)butanoyl]-L-Ser}-1-(Z-L-Phe)-1,5,10-TAD dihydrochloride<br><br>NMR (D$_2$O, external TMS)<br>$\delta$ = 1.4–4.0 (b, 22H), 4.0–4.5 (b, 2H), 4.5–5.0 (b, 2H), 5.33 (s, 2H), 7.65 (s, 14H)<br>IR (Neat)<br>$\nu$ (cm$^{-1}$) = 3390, 2950, 1640, 1445, 1350, 1045<br>TLC (chloroform : methanol : aqueous 17% ammonia solution = 6:4:1 v/v)<br>Rf = 0.37 | 10-{N-[4-(4-GP)butanoyl]-L-Ser}-1-L-Phe-1,5,10-TAD trihydrochloride (Compound No. 5)<br>NMR (D$_2$O, external TMS)<br>$\delta$ = 1.8–4.0 (m, 22H), 4.1–4.5 (b, 3H), 4.6–5.0 (t, 3H, J = 5Hz), 7.5–8.2 (m, 9H)<br><br><br>TLC (chloroform : methanol : aqueous 17% ammonia solution = 6:4:1 v/v)<br>Rf = 0.18<br>$[\alpha]_D^{20}$ −9.5° (C = 1.05, H$_2$O) |
| 6 | 10-{N-[4-(4-GP)butanoyl]-L-Ser}-1-(Aoc-O-tert-butyl-L-Tyr)-1,5,10-TAD dihydrochloride<br>NMR (D$_2$O, external TMS)<br>$\delta$ = 1.0–1.4 (bt, 3H, J = 6Hz), 1.73 (s, 15H), 1.6–4.0 (m, 22H), 4.1–4.5 (d, 2H, J = 5Hz) 4.5–5.0 (m, 2H), 7.1–7.8 (q, 4H, J = 8.5Hz), 7.5–8.0 (m, 4H)<br>IR (KBr)<br>$\nu$ (cm$^{-1}$) = 3290, 2980, 1650, 1510 1440, 1365, 1235, 1155, 1060<br>TLC (chloroform : methanol : aqueous 17% ammonia solution = 6:4:1 v/v)<br>Rf = 0.45 | 10-{N-[4-(4-GP)butanoyl]-L-Ser}-1-L-Tyr-1,5,10-TAD trihydrochloride (Compound No. 6)<br>NMR (D$_2$O, external TMS)<br>$\delta$ = 1.7–4.0 (m, 22H), 4.1–4.4 (d, 2H, J = 5Hz), 4.4–5.0 (m, 2H), 7.2–7.7 (q, 4H, J = 8Hz), 7.5–8.1 (m, 4H)<br><br>IR (KBr)<br>$\nu$ (cm$^{-1}$) = 3250, 2940, 1645, 1510, 1440, 1250, 1055 |
| 7 | 10-{N-[4-(4-GP)butanoyl]-L-Ser}-1-(Z-$\beta$-O-tert-butyl-L-Asp)-1,5,10-TAD dihydrochloride<br><br><br><br><br>IR (KBr)<br>$\nu$ (cm$^{-1}$) = 3240, 1620, 1510, 1240, 1145, 1040<br>TLC (chloroform : methanol : aqueous 17% ammonia solution = 6:4:1 v/v)<br>Rf = 0.43 | $[\alpha]_D^{20}$ +13.7° (C = 1.04, H$_2$O)<br>10-{N-[4-(4-GP)butanoyl]-L-Ser}-1-L-Asp-1,5,10-TAD trihydrochloride (Compound No. 7)<br>NMR (D$_2$O, external TMS)<br>$\delta$ = 1.5–4.0 (m, 22H), 4.1–4.5 (d, 2H, J = 5Hz), 4.5–5.0 (m, 2H), 7.4–8.1 (m, 4H)<br><br><br>TLC (chloroform, methanol, aqueous 17% ammonia solution = 6:4:1 v/v)<br>Rf = 0.23<br><br>$[\alpha]_D^{20}$ −10.2° (C = 1.1, H$_2$O) |

TABLE 6-continued

| Example No. | Compound of general formula [II] | Compound of general formula [I] |
|---|---|---|
| 8 | 10-{N-[4-(4-GP)butanoyl]-L-Ser}-1-(Boc-L-Ala)-1,5,10-TAD dihydrochloride<br><br>NMR (D$_2$O, external TMS)<br>δ = 1.5–4.0 (m, 23H), 1.6–2.0 (d, 3H, J = 7Hz), 1.9 (s, H), 4.1–5.0 (m, 4H), 7.5–8.0 (m, 4H)<br>IR (KBr)<br>ν (cm$^{-1}$) = 3310, 2940, 1635, 1425, 1245, 1150, 1040<br>TLC (chloroform : methanol : aqueous 17% ammonia solution = 6:4:1 v/v)<br>Rf = 0.34 | 10-{N-[4-(4-GP)butanoyl]-L-Ser}-1-L-Ala-1,5,10-TAD trihydrochloride (Compound No. 8)<br><br>NMR (D$_2$O, external TMS)<br>δ = 1.9–2.2 (d, 3H, J = 7Hz), 1.8–4.1 (m, 20H), 4.1–4.5 (d, 2H, J = 5Hz), 4.5–4.9 (m, 2H), 7.5–8.1 (m, 4H)<br>IR (KBr)<br>ν (cm$^{-1}$) = 3290, 2950, 1650, 1540, 1510, 1445, 1255, 1060<br>TLC (chloroform : methanol : aqueous 17% ammonia solution = 6:4:1 v/v)<br>Rf = 0.18<br>[α]$_D^{20}$ −9.1° (C = 0.97, H$_2$O) |
| 9 | 10-{N-[4-(4-GP)butanoyl]-L-Ser}-1-(Z-O-tert-butyl-L-Ser)-1,5,10-TAD dihydrochloride<br>IR (KBr)<br>ν (cm$^{-1}$) = 3300, 2980, 1655, 1525, 1455, 1365, 1255, 1190, 1075<br>TLC (chloroform : methanol : aqueous 17% ammonia solution = 6:4:1 v/v)<br>Rf = 0.31 | 10-{N-[4-(4-GP)butanoyl]-L-Ser}-1-L-Ser-1,5,10-TAD trihydrochloride (Compound No. 9)<br>IR (KBr)<br>ν (cm$^{-1}$) = 3280, 2945, 1650, 1545, 1510, 1455, 1260, 1060<br><br>TLC (chloroform : methanol : aqueous 17% ammonia solution = 6:4:1 v/v)<br>Rf = 0.11<br>[α]$_D^{20}$ −9.2°(C = 1.08, H$_2$O) |
| 10 | 10-{N-[4-(4-GP)butanoyl]-L-Ser}-1-(Boc-L-Pro)-1,5,10-TAD dihydrochloride<br><br>TLC (chloroform : methanol : aqueous 17% ammonia solution = 6:4:1 v/v)<br>Rf = 0.19 | 10-{N-[4-(4-GP)butanoyl]-L-Ser}-1-L-Pro-1,5,10-TAD trihydrochloride (Compound No. 10)<br>TLC (chloroform : methanol : aqueous 17% ammonia solution = 6:4:1 v/v)<br>Rf = 0.23<br>[α]$_D^{20}$ −25.8° (C = 1.04, H$_2$O) |
| 11 | 10-{N-[4-(4-GP)butanoyl]-L-Ser}-1-(Boc-β-Ala)-1,5,10-TAD dihydrochloride<br><br>IR (KBr)<br>ν (cm$^{-1}$) = 3300, 2940, 1645, 1515, 1445, 1365, 1250, 1160, 1055<br>TLC (chloroform : methanol : aqueous 17% ammonia solution = 6:4:1 v/v)<br>Rf = 0.2 | 10-{N-[4-(4-GP)butanoyl]-L-Ser}-1-β-Ala-1,5,10-TAD trihydrochloride (Compound No. 11)<br>IR (KBr)<br>ν (cm$^{-1}$) = 3280, 2950, 1645, 1510, 1450, 1250<br><br><br><br>[α]$_D^{20.5}$ −13.5° (C = 1.02, H$_2$O) |
| 12 | 10-{N-[4-(4-GP)butanoyl]-L-Ser}-1-[(2S, 3R)-3-N-Z-amino-2-hydroxy-4-phenyl-butanoyl]-1,5,10-TAD dihydrochloride<br>IR (KBr)<br>ν (cm$^{-1}$) = 3300, 2950, 1645, 1535, 1445, 1255, 1045<br>TLC (chloroform : methanol : aqueous 17% ammonia solution = 6:4:1 v/v)<br>Rf = 0.34 | 10-{N-[4-(4-GP)butanoyl]-L-Ser}-1-[(2S, 3R)-AHPA]-1,5,10-TAD trihydrochloride (Compound No. 12)<br>IR (KBr)<br>ν (cm$^{-1}$) = 3290, 2945, 1645, 1535, 1515, 1445, 1255, 1065<br>TLC (chloroform : methanol : aqueous 17% ammonia solution = 6:4:1 v/v)<br>Rf = 0.17<br>[α]$_D^{20}$ −18.5° (C = 1.03, H$_2$O) |
| 13 | 10-{N-[4-(4-GP)butanoyl]-L-Ser}-1-(Boc-L-Leu-L-Leu)-1,5,10-TAD dihydrochloride<br>NMR (acetone-d$_6$)<br>δ = 0.6–1.0 (m, 12H), 1.1–4.7 (m, 31H), 1.4 (s, 9H), 6.0–6.6 (b, H), 7.0–7.5 (m, 4H), 7.4–9.0 (b, 10H)<br>IR (KBr)<br>ν (cm$^{-1}$) = 3300, 2950, 1655, 1510, 1365, 1250, 1175, 1130, 1040<br>TLC (chloroform : methanol : aqueous 17% ammonia solution = 6:4:1 v/v)<br>Rf = 0.66 | 10-{N-[4-(4-GP)butanoyl]-L-Ser}-1-L-Leu-L-Leu-1,5,10-TAD trihydrochloride (Compound No. 13)<br>NMR (D$_2$O, external TMS)<br>δ = 1.2–1.7 (m, 6H), 1.7–4.1 (m, 26H), 4.1–5.0 (m, 5H), 7.5–8.1 (m, 4H)<br><br><br>IR (KBr)<br>ν (cm$^{-1}$) = 3290, 2950, 1650, 1545, 1460, 1365, 1255, 1060<br><br>TLC (chloroform : methanol : aqueous 17% ammonia solution 6:4:1 v/v)<br>Rf = 0.14<br>[α]$_D^{20}$ −11.0° (C = 1.05, H$_2$O) |
| 14 | 10-{N-[4-(4-GP)butanoyl]-O-benzyl-L-Ser}-1,5-(di-N-Z-L-PhG)-1,5,10-TAD dihydrochloride<br>NMR (CDCl$_3$)<br>δ = 0.8–3.5 (b, 20H), 3.5–4.1 (b, | 10-{N-[4-(4-GP)butanoyl]-L-Ser}-1,5-di-L-PhG-1,5,10-TAD trihydrochloride (Compound No. 14)<br>NMR (D$_2$O, external TMS)<br>δ = 1.4–4.0 (m, 20H), 4.1–4.5 (d, |

TABLE 6-continued

| Example No. | Compound of general formula [II] | Compound of general formula [I] |
|---|---|---|
| | 2H), 4.3–4.8 (b, H), 4.47 (s, 2H), 5.03 (s, 4H), 5.1–8.1 (b, 11H), 7.33 (s, 29H)<br>IR (KBr)<br>$\nu$ (cm$^{-1}$) = 3300, 2930, 1645, 1515 1450, 1235, 1045,<br>TLC (chloroform : methanol : aqueous 17% ammonia solution = 6 : 1.5 : 0.25 v/v)<br>Rf = 0.28<br>10-{N-[4-(4-GP)butanoyl]-o-t-butyl-L-Ser}-1,5-(di-N-Boc-L-PhG)-1,5,10-TAD* | 2H, J = 5Hz), 4.6–5.0 (t, H, J = 5Hz), 5.5–5.8 (d, H, J = 4Hz), 5.8–6.1 (d, H, J = 4Hz), 7.5–8.1 (m, 4H), 8.03 (s, 5H), 8.06 (s, 5H)<br>IR (KBr)<br>$\nu$ (cm$^{-1}$) = 3270, 3050, 2930, 1640, 1510, 1370, 1250, 1185, 1070, 700<br>TLC (chloroform : methanol : aqueous 17% ammonia solution = 6:4:1 v/v)<br>Rf = 0.47<br>$[\alpha]_D^{20}$ +39.0° (C = 1.01, H$_2$O) |
| 15 | 10-{N-[4-(4-GP)butanoyl]-L-Ser}-1-(Boc-L-Asn)-1,5,10-TAD dihydrochloride<br>IR (KBr)<br>$\nu$ (cm$^{-1}$) = 3300, 2980, 1655, 1515, 1390, 1370, 1250, 1165, 1050<br>TLC (n-propanol : pyridine : water : acetic acid = 6:4:3:2 v/v)<br>Rf = 0.84 | 10-{N-[4-(4-GP)butanoyl]-L-Ser}-1-L-Asn-1,5,10-TAD trihydrochloride (Compound No. 15)<br>IR (KBr)<br>$\nu$ (cm$^{-1}$) = 3300, 2940, 1650, 1550, 1440, 1255, 1060<br><br>$[\alpha]_D^{20}$ −4.3° (C = 1.08, H$_2$O) |
| 16 | 10-{N-[4-(4-GP)butanoyl]-L-Ser}-1-(N$^\alpha$, N$^\epsilon$-di-Z-L-Lys)-1,5,10-TAD dihydrochloride<br>IR (KBr)<br>$\nu$ (cm$^{-1}$) = 3280, 2940, 1645, 1515, 1445, 1245, 1130, 1040<br>TLC (chloroform : methanol : aqueous 17% ammonia solution = 6:4:1 v/v)<br>Rf = 0.22 | 10-{N-[4-(4-GP)butanoyl]-L-Ser}-1-L-Lys-1,5,10-TAD trihydrochloride (Compound No. 16)<br>IR (KBr)<br>$\nu$ (cm$^{-1}$) = 3280, 2940, 1645, 1540, 1515, 1450, 1250, 1055<br>TLC (n-propanol : pyridine : water : acetic acid = 6:4:3:2 v/v)<br>RF = 0.24<br>$[\alpha]_D^{20}$ −3.7° (C = 1.02, H$_2$O) |
| 17 | 10-{N-[4-(4-GP)butanoyl]-Gly}-1-(Boc L-PhG)-1,5,10-TAD dihydrochloride<br>IR (KBr)<br>$\nu$ (cm$^{-1}$) = 3275, 2830, 1660, 1510, 1450, 1360, 1240, 1160<br>TLC (chloroform : methanol : aqueous 17% ammonia solution = 6:4:1 v/v)<br>Rf = 0.16 | 10-{N-[4-(4-GP)butanoyl]-Gly-}-1-L-PhG-1,5,10-TAD trihydrochloride (Compound No. 18)<br>IR (KBr)<br>$\nu$ (cm$^{-1}$) = 3250, 2853, 1642, 1540, 1502, 1450, 1245, 1018<br>TLC (chloroform : methanol : aqueous 17% ammonia solution = 6:4:1 v/v)<br>Rf = 0.52<br>$[\alpha]_D^{20}$ +2.1° (C = 0.95, H$_2$O) |
| 18 | 10-[N-(7-GHep)Gly]-1-(Boc-L-PhG)-1,5,10-TAD dihydrochloride<br><br><br>TLC (chloroform : methanol : aqueous 17% ammonia solution = 6:4:1 v/v)<br>Rf = 0.53 | 10-[N-(7-Ghep)Gly]-1-L-PhG-1,5,10-TAD dihydrochloride (Compound No. 20)<br>IR (KBr)<br>$\nu$ (cm$^{-1}$) = 3250, 3050, 2930, 1645, 1540, 1450, 1370, 1255<br>TLC (chloroform : methanol : aqueous 17% ammonia solution = 6:4:1 v/v)<br>Rf = 0.21<br>$[\alpha]_D^{20}$ +1.6° (C = 1.0, H$_2$O) |
| 19 | 10-[N-(7-GHep)-L-Ser]-1-(Z-L-PhG)-1,5,10-TAD dihydrochloride<br><br>IR (KBr)<br>$\nu$ (cm$^{-1}$) = 3275, 2925, 1640, 1520, 1442, 1240, 1042, 738, 695<br>TLC (chloroform : methanol : aqueous 17% ammonia solution = 6:4:1 v/v)<br>Rf = 0.56 | 10-[N-(7-GHep)-L-Ser]-1-L-PhG-1,5,10-TAD trihydrochloride (Compound No. 22)<br>IR (KBr)<br>$\nu$ (cm$^{-1}$) = 3225, 2925, 1610, 1520, 1450, 1235, 730, 670<br>TLC (chloroform : methanol : aqueous 17% ammonia solution = 6:4:1 v/v)<br>Rf = 0.08<br>$[\alpha]_D^{20}$ +9.8° (C = 1.0, H$_2$O) |
| 20 | 10-{N-[4-(4-GP)butanoyl]-L-Ser}-1-(Boc-L-Pro)-L-Pro)-1,5,10-TAD dihydrochloride<br>IR (KBr)<br>$\nu$ (cm$^{-1}$) = 3280, 2940, 1645, 1540, 1405, 1365, 1250, 1160<br>TLC (chloroform : methanol : aqueous 17% ammonia solution = 6 : 1.5 : 0.25 v/v)<br>Rf = 0.18 | 10-{N-[4-(4-GP)butanoyl]-L-Ser}-1-L-Pro-L-Pro-1,5,10-TAD trihydrochloride (Compound No. 24)<br>IR (KBr)<br>$\nu$ (cm$^{-1}$) = 3280, 2940, 1645, 1535, 1445, 1365, 1250, 1050<br><br>$[\alpha]_D^{20}$ −66.7° (C = 1.08, H$_2$O) |
| 21 | 10-[N-(7-GHep)-L-Ser]-1-(N-Z-$\gamma$-ABA)-1,5,10-TAD dihydrochloride<br>NMR (CD$_3$OD) | 10-[N-(7-GHep)-L-Ser]-1-$\gamma$-ABA-1,5,10, TAD trihydrochloride (Compound No. 25)<br>NMR (CD$_3$OD) |

TABLE 6-continued

| Example No. | Compound of general formula [II] | Compound of general formula [I] |
|---|---|---|
|  | δ = 1.3–1.5 (b, 4H), 1.5–2.0 (m, 12H), 2.2–2.4 (m, 4H), 2.9–3.1 m, 4H), 3.1–3.4 (m, 8H), 3.7–3.9 (d, 2H), 4.3–4.4 (t, H), 5.08 (s, 2H), 7.3 (s, 5H) IR (KBr) ν (cm$^{-1}$) = 3350, 2950, 1650, 1540, 1460, 1380, 1260, 1070 TLC (n-propanol : pyridine : water : acetic acid = 6:4:3:2 v/v) Rf = 0.65 | δ = 1.3–1.5 (b, 4H), 1.5–1.7 (b, 10H), 1.7–2.0 (m, 4H), 2.2–2.4 (m, 4H), 2.7–2.9 (m, 6H), 3.0–3.4 (m, 6H), 3.7–3.8 (m, 2H), 4.2–4.4 (t, H) IR (KBr) ν (cm$^{-1}$) = 3350, 2950, 1660, 1560, 1480, 1380, 1270, 1080, 600 TLC (n-propanol : pyridine : water : acetic acid = 6:4:3:2 v/v) Rf = 0.39 $[\alpha]_D^{20}$ −20.7° (C = 1.0, H$_2$O) |
| 22 | 10-[N-(7-GHep)-L-Ser]-1-(Z-Gly)-1,5,10-TAD dihydrochloride NMR (CD$_3$OD) δ = 1.3–1.5 (b, 4H), 1.5–1.8 (m, 8H), 1.8–2.0 (m, 2H), 2.2–2.4 (t, 2H), 2.8–3.1 (m, 4H), 3.1–3.4 (m, 6H), 3.7–3.9 (m, 4H), 4.25–4.4 (t, H), 5.0–5.2 (s, 2H), 7.2–7.4 (s, 5H) IR (KBr) ν (cm$^{-1}$) = 3350, 2950, 1660, 1540, 1460, 1260, 1060 TLC (n-propanol : pyridine : water : acetic acid = 6:4:3:2 v/v) Rf = 0.58 | 10-[N-(7-GHep)-L-Ser]-1-Gly-1,5,10-TAD trihydrochloride (Compound No. 26) NMR (CD$_3$OD) δ = 1.3–1.5 (b, 4H), 1.5–1.8 (m, 8H), 1.8–2.0 (m, 2H), 2.2–2.4 (t, 2H), 2.9–3.1 (m, 4H), 3.1–3.4 (m, 6H), 3.7 (s, 2H), 3.7–3.8 (m, 2H), 4.3–4.4 (t, H) IR (KBr) ν (cm$^{-1}$) = 3400, 2980, 1680, 1570, 1480, 1290, 1100, 600 TLC (n-propanol : pyridine : water : acetic acid = 6:4:3:2 v/v) Rf = 0.35 $[\alpha]_D^{20}$ −19.5° (C = 1.0, H$_2$O) |
| 23 | 10-[N-(7-GHep)-L-Ser]-1-(Z-γ-OBzl-L-Glu)-1,5,10-TAD dihydrochloride NMR (CD$_3$OD) δ = 1.3–2.2 (m, 25H), 2.2–2.4 (t, 2H), 2.4–2.6 (t, 2H), 2.9–3.4 (m, 10H), 3.7–3.9 (m, 2H), 3.9–4.1 (m, H), 4.3–4.5 (m, H), 5.1–5.2 (s, 2H), 7.2–7.5 (m, 5H) IR (KBr) ν (cm$^{-1}$) = 3350, 2760, 1670, 1550, 1450, 1380, 1260, 1180, 1060 TLC (n-propanol : pyridine : water : acetic acid = 6:4:3:2 v/v) Rf = 0.72 | 10-[N-(7-GHep)-L-Ser]-1-L-Glu-1,5,10-TAD trihydrochloride (Compound No. 27) NMR (CD$_3$OD) δ = 1.4–1.5 (b, 4H), 1.5–1.8 (m, 8H), 1.9–2.0 (m, 2H), 2.0–2.2 (q, 2H), 2.2–2.5 (m, 4H), 3.0–3.2 (m, 4H), 3.2–3.3 (t, 2H), 3.3–3.5 (m, 4H), 3.7–3.9 (m, 2H), 3.9–4.0 (m, H), 4.3–4.4 (m, H) IR (KBr) ν (cm$^{31\,1}$) = 3450, 3000, 1680, 1580, 1490, 1280, 1100 TLC (n-propanol : pyridine : water : acetic acid = 6:4:3:2 v/v) Rf = 0.35 $[\alpha]_D^{20}$ −13.3° (C = 1.0, H$_2$O) |
| 24 | 10-{N-[4-(4-GP)butyryl]-OBzl-L-Ser}-1,5-(di-N-Z-L-Leu)-1,5,10-TAD NMR (CD$_3$OD) δ = 0.6–1.1 (d, 12H, J = 5Hz), 3.9–4.9 (m, 3H), 3.9–7.6 (b, 9H), 4.47 (S, 2H), 5.04 (S, 4H), 6.8–7.4 (m, 4H), 7.26 (S, 15H) IR (KBr) ν (cm$^{-1}$) = 3260, 2930, 1630, 1525, 1445, 1245, 1100, 1035 TLC (chloroform : methanol : 17% ammonia water = 6 : 2.5 : 0.5 v/v) Rf = 0.64 | 10- N-[4-(4-GP)butyryl]-L-Ser]-1,5-(di-N-L-Leu)-1,5,10-TAD trihydrochloride (Compound No. 28) NMR (D$_2$O, external TMS) δ = 1.2–1.8 (bd, 12H, J = 5Hz), 1.8–3.4 (m, 18H), 3.4–4.1 (m, 8H), 4.1–4.4 (d, 2H, J = 6Hz), 4.2–5.0 (m, 3H), 7.5–8.0 (m, 4H) IR (KBr) ν (cm$^{-1}$) = 3240, 2940, 1635, 1510, 1460, 1365, 1255, 1170, 1125, 1060 TLC (chloroform : methanol : 17% ammonia water = 6 : 2.5 : 0.5 v/v) Rf = 0.41 $[\alpha]_D^{20}$ −4.9° (c = 1.02, H$_2$O) |

*Acid (trifluoroacetic acid)-treated at room temperature

REFERENCE EXAMPLE 1

Synthesis of 10-{N-[4-(4-GP)butanoyl]-L-Ser}-1-(Boc-L-Leu)-1,5,10-TAD dihydrochloride (1) 3-(N-Boc-L-Leu)-1,3-thiazolidine-2-thione 10 g (43.23 mmol) of N-Boc-L-leucine was dissolved in 100 ml of methylene chloride. Thereto was added 5.15 g (43.23 mmol) of thiazolidine-2-thione. Further, 8.92 g (43.23 mmol) of dicyclohexylcarbodiimide was added with ice-cooling. The mixture was allowed to react for 6 hours with ice-cooling. The reaction mixture was filtered to remove precipitated N,N'-dicyclohexylurea. The filtrate was concentrated under vacuum to obtain a light yellow crystal. This crystal was suspended in 40 ml of methanol. The suspension was filtered to collect 5.38 g (yield: 41.32%) of the desired compound.

IR (KBr) ν (cm$^{-1}$)=3380, 2930, 1675, 1510, 1335, 1250, 1160, 1040, 845, 755.

(2)
10-{(N-[4-(4-GP)butanoyl]-L-Ser}-1-(Boc-L-Leu)-1,5,10-TAD dihydrochloride 300 mg (0.55 mmol) of a white crystal of 10-{N-[4-(4-GP)butanoyl]-L-Ser}-1,5,10-TAD trihydrochloride was dissolved in 5 ml of methanol. Thereto was added 61.2 mg (0.61 mmol) of triethylamine with ice-cooling. The mixture was allowed to react for 10 minutes with ice-cooling. To the reaction mixture was added 201 mg (0.61 mmol) of the light yellow crystal of 3-(N-Boc-L-Leu)-1,3-thiazolidine-2-thione obtained in the above (1). The resulting mixture was allowed to react for 5 hours at room temperature. The reaction mixture was concentrated under vacuum. The oily residue was suspended in 30 ml of acetone. The supernatant was discarded by decantation, and the same procedure was repeated twice. The residue remained was concentrated under vacuum to obtain 390 mg (yield: 98.2%) of a desired compound as a white crystal.

IR (KBr) $\nu$ (cm$^{-1}$)=3280, 2950, 1640, 1510, 1365, 1250, 1165, 1045.

TLC (chloroform:methanol:aqueous 17% ammonia solution=6:4:1 v/v) Rf=0.39.

In Reference Examples 2 to 4, compounds of the general formula [II] of the Examples except Example 14 were produced from various protected amino acids in the same manner as in Reference Example 1.

REFERENCE EXAMPLE 2

Synthesis of
10-{N-[4-(4-GP)butanoyl]-L-Ser}-1-(Boc-L-Leu-L-Leu)-1,5,10-TAD trihydrochloride 0.84 g (1.28 mmol) of the white crystal of 10-{N-[4-(4-GP)butanoyl]-L-Ser}-1-L-Leu-1,5,10-TAD trihydrochloride obtained in Example 1 was subjected to the same treatment as in Reference Example 1 (2) to obtain the compound of the general formula [II] of Example 13.

REFERENCE EXAMPLE 3

Synthesis of
10-{N-[4-(4-GP)butanoyl]-O-benzyl-L-ser}-1,5-di-(N-Boc-L-PhG)-1,5,10-TAD (1) 10-Boc-1,5,10-TAD 18.9 g (100 mmol) of mono-N-Boc-1,4-butanediamine [see Japanese Patent Application Kokai (Laid-Open) No. 192347/1982] was dissolved in 150 ml of chloroform. Thereto was added 5.57 g (105 mmol) of acrylonitrile with ice-cooling, and the mixture was allowed to react for 3 days at room temperature. The reaction mixture was concentrated under vacuum to obtain 23.4 g of an oily substance.

The oily substance (23.4 g) was dissolved in 260 ml of an ammonia-saturated ethanol. Thereto was added 20 g of Raney nickel, and hydrogenation was effected for 5 hours at room temperature at 60 atm. After the reaction, the reaction mixture was filtered to remove the catalyst. The filtrate was concentrated under vacuum to obtain 23.7 g (yield: 96.7%) of a desired compound as an oily substance.

NMR (D$_2$O, external TMS) $\delta$=1.6–2.5 (m, 6H), 1.9 (s, 9H), 2.7–3.3 (m, 6H), 3.4–3.8 (m, 2H).

(2) 10-Boc-1,5-di-(N-Z-L-PhG)-1,5,10-TAD 2.85 g (11.6 mmol) of the oily 10-Boc-1,5,10-TAD obtained in the above (1) and 6.63 g (23.2 mmol) of N-Z-L-phenylglycine were dissolved in 50 ml of dichloromethane. Thereto was added 5.3 g (27.84 mmol) of 1-ethyl-3-(N,N'-dimethylaminopropyl)-carbodiimide hydrochloride with ice-cooling. The mixture was allowed to react overnight at room temperature. The reaction mixture was concentrated under vacuum to obtain an oily substance. The oily substance was dissolved in 200 ml of ethyl acetate. The solution was washed with an aqueous 5% sodium carbonate solution and an aqueous saturated sodium chloride solution in this order. The organic layer was dried over anhydrous sodium sulfate and then concentrated under vacuum to obtain 10.5 g of an oily substance.

The oily substance was subjected to column chromatography using silica gel 60 manufactured by Merck Co. Development by chloroform followed by elution by a chloroform-methanol (20:1) mixture gave 4.9 g (yield: 54.44%) of an oily substance.

NMR (CDCl$_3$) $\delta$=0.9–1.9 (m, 6H), 1.47 (s, 9H), 2.7–3.8 (m, 8H), 4.5–5.0 (b, H), 5.2–6.0 (m, 2H), 5.23 (s, 4H), 6.1–6.6 (b, 2H), 6.9–8.0 (b, H), 7.5 (s, 10H), 7.53 (s, 10H).

TLC (chloroform:methanol=10:1 v/v) Rf=0.49.

(3) 1,5-Di-(N-Z-L-PhG)-1,5,10-TAD 4.9 g (6.28 mmol) of the 10-Boc-1,5-di(N-Z-L-PhG)-1,5,10-TAD obtained in the above (2) was dissolved in 20 ml of trifluoroacetic acid with ice-cooling. The solution was allowed to react for 2 hours. The reaction mixture was concentrated under vacuum to obtain an oily substance. The oily substance was dissolved in 150 ml of ethyl acetate, and the solution was washed with an aqueous 5% sodium carbonate solution and a saturated aqueous sodium chloride solution in this order. The organic layer was dried over anhydrous sodium sulfate and then concentrated under vacuum to obtain 4.4 g (yield: quantitative) of a desired compound as an oily substance.

IR (KBr) $\nu$ (cm$^{-1}$)=3290, 3030, 2920, 1700, 1635, 1490, 1445, 1325, 1230, 1145, 1035.

TLC (chloroform:methanol=1:1 v/v) Rf=0.12.

(4)
10-(N-Boc-O-benzyl-L-Ser)-1,5-di-(N-Z-L-PhG)-1,5,10-TAD 3.2 g (4.7 mmol) of the 1,5-di-(N-Z-L-PhG)-1,5,10-TAD obtained in the above (3) was dissolved in 40 ml of dichloromethane. Thereto was added 0.8 g (7.9 mmol) of triethylamine with ice-cooling. Further, 2.39 g (6.09 mmol) of N-Boc-O-benzyl-L-serine N-hydroxysuccinimide ester was added. The mixture was allowed to react overnight at room temperature. The reaction mixture was concentrated under vacuum and the residue was dissolved in 200 ml of ethyl acetate. The solution was washed with 5% phosphoric acid, an aqueous 5% sodium carbonate solution and a saturated aqueous sodium chloride solution in this order. The organic layer was dried over anhydrous sodium sulfate and then filtered to remove the drying agent. The filtrate was concentrated under vacuum to obtain 4.2 g (yield: 93.3%) of a desired compound as a light yellow oily substance.

IR (KBr) $\nu$ (cm$^{-1}$)=3305, 2930, 1705, 1650, 1495, 1450, 1300, 1235, 1160, 1040.

TLC (chloroform:methanol=20:1 v/v) Rf=0.43.

(5)
10-(O-Benzyl-L-Ser)-1,5-di-(N-Z-L-PhG)-1,5,10-TAD 4.2 g (4.38 mmol) of the 10-(N-Boc-O-benzyl-L-Ser)-1,5-di-(N-Z-L-PhG)-1,5,10-TAD obtained in the above (4) was dissolved in 20 ml of trifluoroacetic acid with ice cooling. The solution was allowed to react for 2 hours. The reaction mixture was concentrated under vacuum to obtain an oily substance. This substance was dissolved in 150 ml of ethyl acetate and washed with an aqueous 5% sodium carbonate solution and a saturated aqueous sodium chloride solution in this order. The organic layer was dried over anhydrous sodium sulfate, and then filtered to remove the drying agent. The filtrate was concentrated under vacuum to obtain 3.7 g (yield: quantitative) of a desired compound as an oily substance.

IR (KBr) $\nu$ (cm$^{-1}$)=3305, 2930, 1710, 1640, 1520, 1495, 1450, 1325, 1235, 1075, 1040.

TLC (chloroform:methanol=10:1 v/v) Rf=0.13.

(6)
10-{N-[4-(4-GP)butanoyl]-O-benzyl-L-Ser}-1,5-di(N-Z-L-PhG)-1,5,10-TAD hydrochloride 1.2 g (5.42 mmol) of a brown crystal of 4-(4-GP)butyric acid was added to 7 ml of ice-cooled thionyl chloride, in 4 to 5 portions. The mixture was allowed to react for 15 minutes. The reaction mixture was concentrated to dryness under vacuum.

3.8 g (4.38 mmol) of the 10-(O-benzyl-L-Ser)-1,5-di(N-Z-L-PhG)-1,5,10-TAD obtained in the above (5) was dissolved in 30 ml of dimethylformamide. Thereto was added 0.65 g (8.21 mmol) of pyridine with ice-cooling. There was further added a solution obtained by dissolving a hydrochloride of the above prepared 4-(4-GP)-butyric chloride in 7 ml of dimethylformamide. The mixture was allowed to react for 30 minutes with ice-cooling. The reaction mixture was concentrated under vacuum to obtain an oily residue. The residue was dissolved in a mixture consisting of 300 ml of ethyl acetate and 90 ml of ethanol and the mixture was washed with 5% phosphoric acid, an aqueous 5% sodium carbonate solution and a saturated aqueous sodium chloride solution in this order. Since a slight amount of an oily substance precipitated during washing, ethanol was added to dissolve the precipitate. The organic layer was dried over anhydrous sodium sulfate and then filtered to remove the drying agent. The filtrate was concentrated under vacuum to obtain 4.8 g (yield: quantitative) of a desired compound as a light yellow oily substance.

IR (KBr) $\nu$ (cm$^{-1}$)=3300, 2930, 1645, 1515, 1450, 1235 1045.

TLC (chloroform:methanol:aqueous 17% ammonia solution=6:1.5:0.25 v/v) RF=0.28.

REFERENCE EXAMPLE 4

Synthesis of 10-{N-[4-(4-GP)butanoyl]-L-Ser}-1-(Z-L-PhG)-1,5,10-TAD dihydrochloride (1) 3-(N-Z-L-PhG)-1,3-thiazolidine-2-thione 5.7 g (20 mmol) of N-Z-L-phenylglycine was dissolved in 50 ml of methylene chloride. Thereto was added 2.38 g (20 mmol) of 1,3-thiazolidine-2-thione. Further, 4.13 g (20 mmol) of dicyclohexylcarbodiimide was added with ice cooling. The mixture was allowed to react for 6 hours with ice-cooling. The reaction mixture was filtered to remove N,N'-dicyclohexylurea. The filtrate was concentrated under vacuum to obtain 12.0 g of a light yellow oily substance. The substance was chromatographed on a column packed with silica gel ® 60 manufactured by Merck Co. Development was conducted using a mixed solvent, n-hexane-chloroform-ethyl acetate (6:3:1-2 v/v) mixture, whereby 4.0 g (yield: 1.28%) of a desired compound was obtained as a light yellow oily substance.

IR (KBr) $\nu$ (cm$^{-1}$)=3390, 1690, 1585, 1500, 1455, 1335, 1275, 1225, 1170, 1055.

TLC (n-hexane:chloroform:ethyl acetate=6:3:2 v/v) Rf=0.28.

(2)
10-{N-[4-(4-GP)butanoyl]-L-Ser}-1-(Z-L-PhG)-1,5,10-TAD dihydrochloride 0.55 g (1 mmol) of a white crystal of 10-{N-[4-(4-GP)butanoyl]-L-Ser}-1,5,10-TAD trihydrochloride was dissolved in 6 ml of methanol. Thereto was added 0.106 g (1.05 mmol) of triethylamine with ice-cooling.

The mixture was allowed to react for 10 minutes with ice-cooling. To the reaction mixture was added 0.41 g (1.05 mmol) of the light yellow oily substance of 3-(N-Z-L-PhG)-1,3-thiazolidine-2-thione obtained in the above (1). The mixture was allowed to react for 5 hours at room temperature. The reaction mixture was concentrated under vacuum. The oily residue was suspended in 30 ml of acetone. The supernatant was discarded by decantation. The same procedures was repeated twice. The residue was dried under vacuum to obtain 0.83 g (yield: quantitative) of a desired compound as a white crystal.

IR (KBr) $\nu$ (cm$^{-1}$)=3270, 1620, 1510, 1235, 1040.

TLC (chloroform:methanol:aqueous 17% ammonia solution=6:4:1 v/v) Rf=0.51.

Various other compounds of the general formula [II] can be produced from various protected amino acids in the same manner as in Reference Example 1.

When the product obtained in Reference Example 1 (1) is a light yellow crystal, further purification with column chromatography is not necessary. The crystal is suspended in methanol and is recovered by filtration, whereby a desired compound can be obtained with high purity.

What is claimed is:

1. A spergualin-related compound represented by the formula [I]

$$\begin{array}{c} H_2N \\ \diagdown \\ C-NH-X-(CH_2)_3-CONHCHCONH- \\ \diagup \\ HN \end{array} \begin{array}{c} R \\ | \\ \end{array} [I]$$

$$\begin{array}{c} R_1 \\ | \\ -(CH_2)_4-N-(CH_2)_3-NH-R_2 \end{array}$$

wherein X is $$-(CH_2)_{3-5}- \text{ or } -\!\!\!\bigcirc\!\!\!-\!\!;$$

R is —H or —CH$_2$OH; R$_1$ is —H, R$_2$ is a residue obtained by removing, from an amino acid or peptide, the hydroxyl group of the alpha-carboxyl group, or a pharmaceutically acceptable salt thereof.

2. A compound or a pharmaceutically acceptable salt thereof according to claim 1, wherein $R_2$ of formula [I] is (1) a group represented by the formula

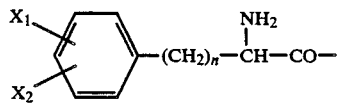

wherein n is 0 or 1; $X_1$ is —H or —OH; and $X_2$ is —H or —CH$_2$OH, (2) a group represented by the formula

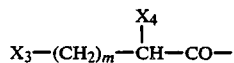

wherein m is an integer of 0 to 4; $X_3$ is —H, —COOH, —OH, —NH$_2$ or —CONH$_2$; $X_4$ is —H or —NH$_2$; and at least one of $X_3$ and $X_4$ is —NH$_2$, (3) a group represented by the formula

wherein y is 1 or 2; A is

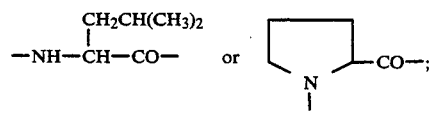

and, when y is 2, two A's form a peptide linkage, or (4) a group represented by the formula

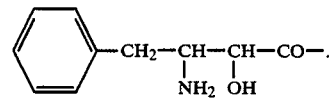

3. A compound or a pharmaceutically acceptable salt thereof according to claim 1, wherein X of the formula [I] is

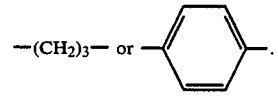

4. A compound or a pharmaceutically acceptable salt thereof according to claim 1, in wherein formula [I], X is

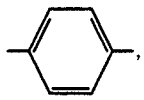

R is —CH$_2$OH, $R_1$ is —H, and $R_2$ is

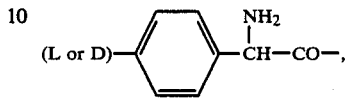

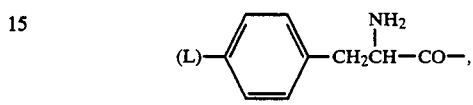

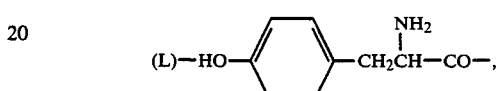

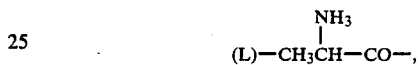

(L)—CH$_3$CH—CO—,

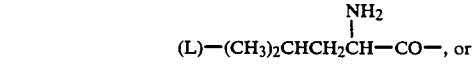

(L,L)—(CH$_3$)$_2$CHCH$_2$CHCO—NH—CH—CO—
 |   |
 NH$_2$   CH$_2$CH(CH$_3$)$_2$

5. A novel spergualin-related compound represented by the formula [II]

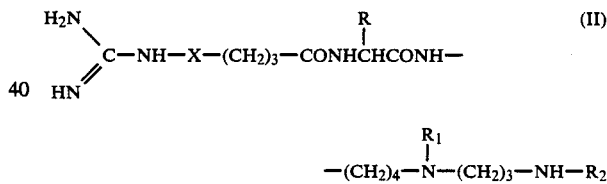

wherein X is

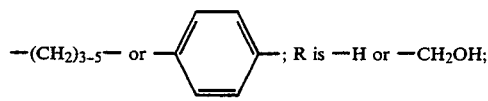; R is —H or —CH$_2$OH;

$R_1$ and $R_2$ represent 

or (CH$_3$)$_2$—CHCH$_2$—CH—CO—,
                |
                NH$_2$ or a pharmaceutically acceptable salt thereof.

6. The compound of the formula

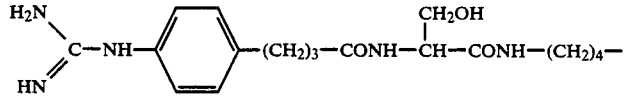

-continued
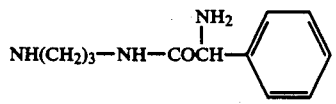
or a pharmaceutically acceptable salt thereof.
7. The compound of the formula
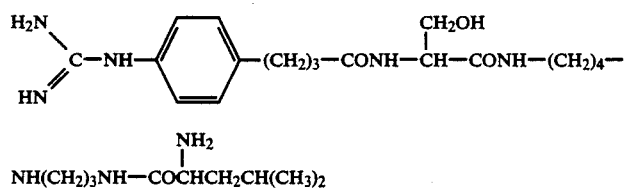
or a pharmaceutically acceptable salt thereof.
8. The compound of the formula
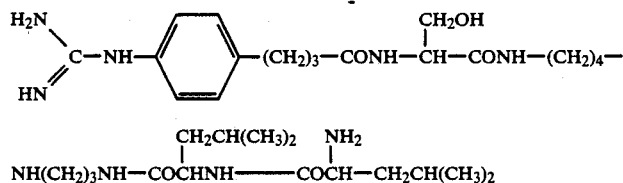
or a pharmaceutically acceptable salt thereof.
9. The compound of the formula
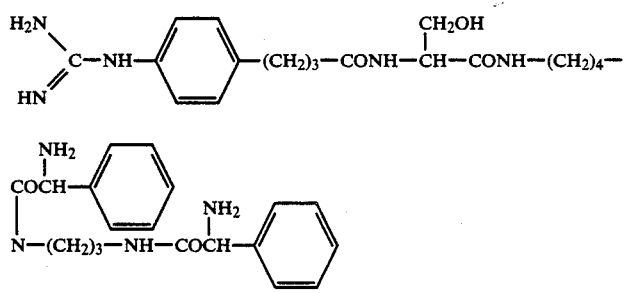
10. The compound of the formula
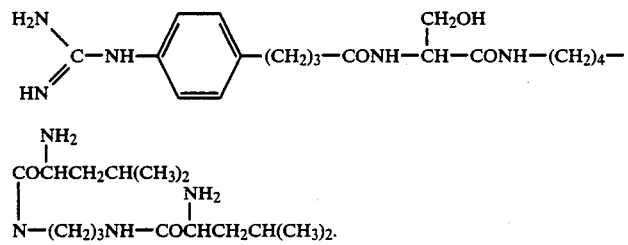
* * * * *